United States Patent [19]

Fankhauser et al.

[11] Patent Number: 5,214,163
[45] Date of Patent: May 25, 1993

[54] PROCESS FOR THE PREPARATION OF 15-PENTADECANOLIDE OR OF MIXTURES RICH IN THIS MACROLIDE

[75] Inventors: Peter Fankhauser, Meyrin; Piero Fantini, Geneva, both of Switzerland

[73] Assignee: Firmenich S.A., Geneva, Switzerland

[21] Appl. No.: 836,489

[22] Filed: Feb. 18, 1992

[30] Foreign Application Priority Data

Mar. 13, 1991 [CH] Switzerland .............................. 766/91

[51] Int. Cl.$^5$ .......................................... C07D 311/02
[52] U.S. Cl. ...................................... 549/396; 512/11
[58] Field of Search ........................... 512/11; 549/396

[56] References Cited

U.S. PATENT DOCUMENTS

| | | | |
|---|---|---|---|
| 3,890,353 | 6/1975 | Becker | 549/396 |
| 3,907,831 | 9/1975 | Becker | 549/396 |
| 3,925,421 | 12/1975 | Story et al. | 512/11 |
| 4,568,470 | 2/1986 | Van Loveren et al. | 512/11 |

FOREIGN PATENT DOCUMENTS

| | | | |
|---|---|---|---|
| 55-81875 | 6/1980 | Japan | 512/11 |
| 7407462 | 8/1974 | Netherlands | 512/11 |
| 7407463 | 8/1974 | Netherlands | 512/11 |

*Primary Examiner*—James H. Reamer
*Attorney, Agent, or Firm*—Pennie & Edmonds

[57] ABSTRACT

A process for the preparation of 15-pentadecanolide, wherein bis-(13-oxabicyclo[10.4.0]hexadec-12-yl)peroxide is subjected to a thermal treatment in an organic solvent, eventually followed by hydrogenation of the resulting reaction product, which treatment is carried out in an organic solvent having a boiling point comprised between about 170° and 250° C.

6 Claims, No Drawings

PROCESS FOR THE PREPARATION OF 15-PENTADECANOLIDE OR OF MIXTURES RICH IN THIS MACROLIDE

BRIEF SUMMARY OF THE INVENTION

The present invention relates to a process for the preparation of 15-pentadecanolide, or of a mixture of 15-pentadecanolide and 15-pentadec-11(12)-enolide, by means of a thermal treatment of bis-(13-oxabicyclo[10.4.0]hexadec-12-yl)peroxide in an organic solvent, which process comprises using an organic solvent having a boiling point comprised in between about 170° and 250° C.

The invention further relates to a method to confer, enhance, improve or modify the odor properties of a perfuming composition or a perfumed article, which method comprises adding to said composition or article a fragrance effective amount of 15-pentadecanolide, or of a mixture of 15-pentadecanolide and 15-pentadec-11(12)-enolide, such as obtained by the above-mentioned process.

BACKGROUND OF THE INVENTION

The present invention relates to the field of organic synthesis and concerns, in particular, an improved process for the preparation of 15-pentadecanolide. The latter is lactone well-appreciated in perfumery for its musky odor.

It is known from the prior art [see, for example, patent FR 70 19709 or patents U.S. Pat. Nos. 3,907,831 and 3,890,353] to prepare 15-pentadecanolide and some of its derivatives by means of a thermolysis of a peroxide of formula $R'^1$—O—O—$R'^2$, $R'^1$ represent a group of formula

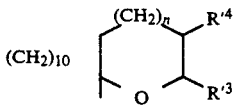

and $R'^2$ represents a hydrogen, a hydrocarbon, an acyl group or a second group of the above-cited formula. In the latter $R'^3$ and $R'^4$ stand for hydrogen, or one of these symbols represents a methyl radical and the other hydrogen, and n stands for an integer of value 0 to 3. As described in the cited prior art, said thermolysis is carried out in an organic solvent at a temperature comprised between 80° and 150° C. and is followed by hydrogenation of the resulting reaction product. Amongst the peroxides used as starting products in the cited process, there is described bis-(13-oxbicyclo[10.4.0]hexadec-12-yl)peroxide. As the medium in which the thermolysis is carried out, there are described, in the prior art documents, solvents which have a boiling point falling in the range of temperatures comprised between 80° and 150°. Liquid aromatic hydrocarbons, such as toluene, xylene and mixtures of o-, m- and p-xylene, are cited as preferred solvents and all the described examples cite xylene as the solvent used. The reaction product, after distillation, consisted of a mixture rich in 15-pentadecanolide. This mixture was then systematically hydrogenated to yield 15-pentadecanolide which was thus freed of its unsaturated homologue, i.e. 15-pentadec-11(12)-enolide.

One of the disadvantages of this prior art process was the fact that the yield of the thermolysis reaction in the mixture of lactones, measured relative to the starting peroxide, was never above 60% and was often below this value. Another disadvantage resided in the fact that 15-pentadecanolide, obtained by hydrogenation of the mixture of lactones, was accompanied of by-products whose separation was laborious and expensive, thus entailing additional costs and reducing the industrial usefulness of the process.

THE INVENTION

We have now discovered unexpectedly that the cited disadvantages of the prior art process could be counteracted by using specific solvents in the thermal treatment of the starting peroxide, particularly when bis-(13-oxabicyclo[10.4.0]hexadec-12-yl)peroxide was used as the starting product.

The solvents concerned in the present invention are organic solvents which have a boiling point comprised between about 170° and 250° C. The reaction is carried out by thermolysis at a temperature of approximately 140° C., or above, say at the boiling point or close to the boiling point of the chosen solvent.

According to a preferred embodiment of the process of the invention, the thermolysis is carried out at a temperature comprised in the range of about 140°-200° C.

Amongst the preferred solvents, there can be cited the aromatic derivatives obeying the formula

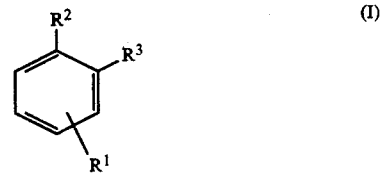

wherein
a. symbols $R^1$ and $R^3$ represent each an isopropyl radical and symbol $R^2$ stands for a hydrogen atom, $R^1$ being in meta or para position relative to $R^3$;
b. symbols $R^1$ and $R^2$ represent each a hydrogen atom and symbol $R^3$ stands for a —CH(CH$_3$)$_2$, —CH$_2$NH$_2$, —CH$_2$—NHCH$_3$, —CH$_2$—N(CH$_3$)$_2$, —CH$_2$OCOCH$_3$, —CH$_2$CN, —COCH$_3$, —N(C$_2$H$_5$)$_2$ or —CH$_2$OH radical;

or c. symbol $R^1$ represents a hydrogen atom and symbols $R^2$ and $R^3$, together with the carbon atoms to which they are bonded, form a cycloaliphatic nucleus.

As compounds defined by means of formula (I) one can cite m- and p-diisopropylbenzene, benzyl alcohol, benzyl acetate, acetophenone, benzylamine, N,N-diethylaniline, N-methylbenzylamine, N,N-dimethylbenzylamine, phenylacetonitrile or 1,2,3,4-tetrahydronaphthalene.

Other solvents having a boiling point comprised in between the limits indicated above can also be conveniently used. These include furfuryl alcohol, methyl succinate, N-methylpyrrolidone, methyl acetoacetate, 2-pentylcyclopentanone or yet triglyme (triethylene glycol dimethyl ether).

Amongst the variety of chosen solvents, 1,2,3,4-tetrahydronaphthalene is preferably employed, either on its own, or in admixture with one or more of the other solvents cited, for example in admixture with a nitrogen base such as N,N-diethylaniline.

The thermolysis reaction is carried out in the manner described in the cited prior art documents, hereby included by reference. According to a particular embodiment of the invention, the process will also comprise the subsequent hydrogenation of the obtained thermolysis mixture and said hydrogenation is also carried out in the usual manner. The specific conditions of these reactions will be described in detail in the examples presented further on.

Bis-(13-oxabicyclo[10.4.0]hexadec-12-yl)peroxide, i.e. the starting product of the process according to the invention, can be prepared as described in the prior art [see cited documents].

The process according to the present invention makes it possible to improve, in a remarkable way, the yield in lactone mixture obtained after the thermal treatment of peroxide (I), as it is evident from the examples presented further on. Furthermore, we observed with surprise that, thanks to the process of the invention, we could obtain mixtures whose proportion in 15-pentadecanolide, relative to its unsaturated homologue 15-pentadec 11(12)-enolide, was higher than that of the mixtures obtained according to the prior art process. We were able to obtain, in fact, mixtures having a content in 15-pentadec-11(12)-enolide inferior to 10% by weight, relative to the weight of the mixture. This result is very interesting since, for certain perfumery applications of 15-pentadecanolide, these mixtures were considered adequate and could replace said macrolide, thus rendering superfluous the step of hydrogenation heretofore indispensable for obtaining a good quality of 15-pentadecanolide. On the other hand, if nevertheless one still desires to carry out the hydrogenation of the mixture obtained by the process of the invention, we have observed that the yield in 15-pentadecanolide is far better and that the separation of this lactone by distillation is easier and more economic than in the prior art process.

In view of the prior art cited, these results are totally surprising and unexpected. In effect, the organic solvents concerned in the process of the invention have a boiling point above the value recommended in the prior art documents and the man in the art, relying on this prior art, would not have had any particular reason to resort to these solvents, he would in fact have been discouraged from doing so.

As indicated above, the mixtures of 15-pentadecanolide and 15-pentadec-11(12)-enolide, containing less than 10% by weight of the latter, relative to the weight of the mixture, obtained by the described process, are useful as intermediate products for the preparation of 15-pentadecanolide. They are also useful as perfuming ingredients and can successfully replace 15-pentadecanolide in perfuming compositions and perfumed articles.

The invention will now be described in greater detail by way of the following examples, wherein the temperatures are indicated in degrees centigrade and the abbreviations have the usual meaning in the art.

EXAMPLE 1

The reaction was carried out in a 4-neck 2l reactor, modified by adjunction of a lateral output allowing continuous drawing off. The reactor was equipped with:
a double-mantel introduction tube, water-cooled,
a reflux condenser, water-cooled,
a mechanical stirrer,
a temperature probe,
a nitrogen inlet.

250 Ml of 1,2,3,4-tetrahydronaphthalene were charged into the reactor maintained under nitrogen and were heated to 140°, under vigorous stirring. 77.2 G (0.127 mol) of bis-(13-oxabicyclo[10.4.0]hexadec-12-yl)peroxide in suspension in 1200 ml of 1,2,3,4-tetrahydronaphthalene were then added by means of a dosing pump to the preheated 1,2,3,4-tetrahydronaphthalene, while maintaining the temperature at about 140°. After approximately 20 min, the reaction solution was recovered by drawing off through the lateral outlet of the reactor, the output flow being controlled by the flow of addition of the peroxide suspension. Once the addition was completed, the dosing pump was rinsed by means of 150 ml of 1,2,3,4-tetrahydronaphthalene, while the contents of the reactor were kept at 140° for another 10 min. After cooling, the contents of the reactor were combined with the drawn-off reaction solution. The mixture of the desired lactones was finally separated by fraction distillation by means of an apparatus equipped with a Vigreux column (yield 73%).

EXAMPLE 2

Using the same type of reactor as that described in example 1, thermolysis of 85 g (0.178 mol) of bis-(13-oxabicyclo[10.4.0]hexadec-12-yl)peroxide was carried out, employing as solvent m-diisopropylbenzene (1200 ml) instead of 1,2,3,4-tetrahydronaphthalene. The yield in the mixture of the desired lactones was 63% Proceeding in an analogous way, but using the solvents indicated hereinafter, the yields described in the following table were obtained.

TABLE

| Essay N° | Solvent | Yield [%] | B.p.[1] [°C.] |
|---|---|---|---|
| 1 | p-diisopropylbenzene | 59 | 210 |
| 2 | benzyl alcohol | 69 | 205 |
| 3 | benzyl acetate | 53 | 206 |
| 4 | acetophenone | 51 | 202 |
| 5 | N,N-diethylaniline | 62 | 217 |
| 6 | benzylamine | 70 | 184 |
| 7 | N-methylbenzylamine | 70 | 185 |
| 8 | N,N-dimethylbenzylamine | 61 | 180 |
| 9 | phenylacetonitrile | 70 | 232 |
| 10 | furfuryl alcohol | 37 | 170 |
| 11 | methyl succinate | 58 | 192 |
| 12 | N-methylpyrrolidone | 70 | 202 |
| 13 | methylacetoacetate | 61 | 170 |
| 14 | 2-pentylcyclopentanone | 64 | 220 |
| 15 | triglyme[2] | 51 | 225 |
| 16 | tetrahydronaphthalene + 2% N,N-diethylaniline | 74 | 207 (217) |

[1] boiling point of the chosen solvent in °C. at ordinary pressure
[2] triethylene glycol dimethyl ether.

What we claim is:

1. A process for preparing 15-pentadecanolide, or a mixture of 15-pentadecanolide and 15-pentadec-11(12)-enolide, which comprises thermally treating bis-(13-oxabicyclohexadec-12yl)peroxide in an organic solvent of 1,2,3,4-tetrahydronaphthalene for a sufficient time and at a temperature sufficient to obtain 15-pentadecanolide or mixtures which predominantly contain 15-pentadecanolide.

2. A process according to claim 1, wherein the reaction product obtained after the thermal treatment is submitted to a subsequent hydrogenation.

3. A process according to claim 1, wherein the thermal treatment is carried out at a temperature between 140° and 200° C.

4. A process according to claim 1, wherein the solvent is a mixture of 1,2,3,4-tetrahydronaphthalene with an amine.

5. A process according to claim 4, wherein the amine is N,N-diethylaniline.

6. The process of claim 1 which further comprises preparing a mixture of 15-pentadecanolide and 15-pentadec11(12)-enolide, wherein the mixture contains less than 10% by weight of 15-pentadec-11(12)-enolide, relative to the weight of the mixture.

* * * * *

UNITED STATES PATENT AND TRADEMARK OFFICE
CERTIFICATE OF CORRECTION

PATENT NO. : 5,214,163

DATED : May 25, 1993

INVENTOR(S) : Peter Fankhauser and Piero Fantini

It is certified that error appears in the above-indentified patent and that said Letters Patent is hereby corrected as shown below:

Column 1, line 28, should read: "The latter is a lactone..."

formula, line 40, should be:

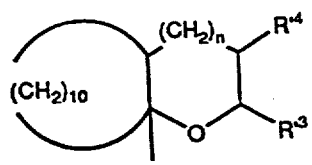

Column 4, lines 57/58, should read: "...bis-(13-oxabicyclo[10.4.0]hexadec-12-yl)peroxide..."

Column 6, lines 2/3, should read: --15-pen-tadec-11(12)-enolide,--.

Signed and Sealed this

Thirteenth Day of June, 1995

Attest:

BRUCE LEHMAN

Attesting Officer  Commissioner of Patents and Trademarks